(12) United States Patent
Banet et al.

(10) Patent No.: US 7,993,275 B2
(45) Date of Patent: Aug. 9, 2011

(54) BILATERAL DEVICE, SYSTEM AND METHOD FOR MONITORING VITAL SIGNS

(75) Inventors: Matthew John Banet, Del Mar, CA (US); Michael James Thompson, San Diego, CA (US); Zhou Zhou, La Jolla, CA (US); Henk Visser, II, San Diego, CA (US)

(73) Assignee: Sotera Wireless, Inc., San Diego, CA (US)

( * ) Notice: Subject to any disclaimer, the term of this patent is extended or adjusted under 35 U.S.C. 154(b) by 1388 days.

(21) Appl. No.: 11/420,281

(22) Filed: May 25, 2006

(65) Prior Publication Data

US 2007/0276261 A1 Nov. 29, 2007

(51) Int. Cl.
*A61B 5/02* (2006.01)

(52) U.S. Cl. ........................................ 600/485; 600/500

(58) Field of Classification Search .................... 600/504
See application file for complete search history.

(56) References Cited

U.S. PATENT DOCUMENTS

| | | | |
|---|---|---|---|
| 3,412,729 A | 11/1968 | Smith | |
| 4,063,551 A | 12/1977 | Sweeney | |
| 4,080,966 A | 3/1978 | McNally et al. | |
| 4,245,648 A | 1/1981 | Trimmer et al. | |
| 4,320,767 A | 3/1982 | Villa-Real | |
| 4,367,752 A | 1/1983 | Jimenez et al. | |
| 4,380,240 A | 4/1983 | Jobsis et al. | |
| 4,425,920 A | 1/1984 | Bourland et al. | |
| 4,681,118 A | 7/1987 | Asia et al. | |
| 4,777,954 A | 10/1988 | Kuesch et al. | |
| 4,825,879 A | 5/1989 | Tan et al. | |
| 4,846,189 A | 7/1989 | Sun | |
| 4,869,261 A | 9/1989 | Penaz | |
| 4,917,108 A | 4/1990 | Mault | |
| 5,002,055 A | 3/1991 | Merki et al. | |
| 5,038,792 A | 8/1991 | Mault | |
| 5,054,494 A | 10/1991 | Lazzaro et al. | |
| 5,111,817 A | 5/1992 | Clark et al. | |

(Continued)

OTHER PUBLICATIONS

Assessment of Vasoactive Agents and Vascular Aging by the Second Derivative of Photoplethysmogram Waveform', Takazawa et. al, Hypertension 32: 365-370, 1998.

(Continued)

*Primary Examiner* — Patricia Mallari
(74) *Attorney, Agent, or Firm* — Wilmer Cutler Pickering Hale & Dorr LLP.

(57) ABSTRACT

The invention features a monitoring device that measures a patient's vital signs (e.g. blood pressure). The device features a first sensor configured to attach to a first portion of the patient's body that includes: i) a first electrode configured to generate a first electrical signal from the first portion of the patient's body; ii) a first light-emitting component; and iii) a first photodetector configured to receive radiation from the first portion of the patient's body after the radiation is emitted by the first light-emitting component and in response generate a first optical waveform. The device also features a second sensor that includes essentially the same components. An amplifier system, in electrical contact with the first and second electrodes, receives first and second electrical signals from the two sensors to generate an electrical waveform. A processor, in electrical contact with the amplifier system, receives the electrical waveform, the first optical waveform, and the second optical waveform. The processor runs computer code that processes the input waveforms with an algorithm to determine at least one of the patient's vital signs.

22 Claims, 8 Drawing Sheets

U.S. PATENT DOCUMENTS

| | | | |
|---|---|---|---|
| 5,140,990 A | 8/1992 | Jones et al. | |
| 5,178,155 A | 1/1993 | Mault | |
| 5,179,958 A | 1/1993 | Mault | |
| 5,213,099 A | 5/1993 | Tripp, Jr. | |
| 5,237,997 A | 8/1993 | Greubel et al. | |
| 5,309,916 A * | 5/1994 | Hatschek | 600/485 |
| 5,316,008 A | 5/1994 | Suga et al. | |
| 5,368,039 A | 11/1994 | Moses | |
| 5,431,170 A * | 7/1995 | Mathews | 600/479 |
| 5,435,315 A * | 7/1995 | McPhee et al. | 600/483 |
| 5,485,848 A | 1/1996 | Jackson et al. | |
| 5,551,438 A | 9/1996 | Moses | |
| 5,632,272 A | 5/1997 | Diab et al. | |
| 5,727,558 A | 3/1998 | Hakki et al. | |
| 5,743,857 A | 4/1998 | Shinoda et al. | |
| 5,788,634 A | 8/1998 | Suda et al. | |
| 5,836,300 A | 11/1998 | Mault | |
| 5,857,975 A | 1/1999 | Golub | |
| 5,865,755 A | 2/1999 | Golub | |
| 5,865,758 A | 2/1999 | Louzianine | |
| 5,891,042 A | 4/1999 | Sham et al. | |
| 5,921,936 A | 7/1999 | Inukai et al. | |
| 6,004,274 A | 12/1999 | Nolan et al. | |
| 6,013,009 A | 1/2000 | Karkanen | |
| 6,050,940 A | 4/2000 | Braun et al. | |
| 6,176,831 B1 | 1/2001 | Voss et al. | |
| 6,224,548 B1 | 5/2001 | Gopinathan et al. | |
| 6,245,014 B1 | 6/2001 | Brainard, II | |
| 6,272,936 B1 | 8/2001 | Oreper | |
| 6,280,390 B1 | 8/2001 | Akselrod et al. | |
| 6,331,162 B1 | 12/2001 | Mitchell | |
| 6,334,065 B1 | 12/2001 | Al-Ali et al. | |
| 6,336,900 B1 | 1/2002 | Alleckson et al. | |
| 6,364,842 B1 | 4/2002 | Amano et al. | |
| 6,371,921 B1 | 4/2002 | Caro et al. | |
| 6,375,614 B1 | 4/2002 | Braun et al. | |
| 6,398,727 B1 | 6/2002 | Bui et al. | |
| 6,413,223 B1 | 7/2002 | Yang et al. | |
| 6,432,061 B1 | 8/2002 | Nissila et al. | |
| 6,443,905 B1 | 9/2002 | Nissila et al. | |
| 6,443,906 B1 | 9/2002 | Ting et al. | |
| 6,472,617 B1 * | 10/2002 | Montagnino | 177/126 |
| 6,475,146 B1 | 11/2002 | Frelburger et al. | |
| 6,475,153 B1 | 11/2002 | Khair et al. | |
| 6,477,397 B1 | 11/2002 | Ronkainen et al. | |
| 6,511,436 B1 * | 1/2003 | Asmar | 600/500 |
| 6,514,211 B1 | 2/2003 | Baura | |
| 6,527,711 B1 | 3/2003 | Stivoric et al. | |
| 6,533,729 B1 | 3/2003 | Khair et al. | |
| 6,546,269 B1 | 4/2003 | Kurnik | |
| 6,553,247 B1 | 4/2003 | Rytky | |
| 6,556,852 B1 | 4/2003 | Schulze et al. | |
| 6,558,321 B1 | 5/2003 | Burd et al. | |
| 6,571,200 B1 | 5/2003 | Mault | |
| 6,595,929 B2 | 7/2003 | Stivoric et al. | |
| 6,599,251 B2 | 7/2003 | Chen et al. | |
| 6,605,038 B1 | 8/2003 | Teller et al. | |
| 6,605,044 B2 | 8/2003 | Bimbaum | |
| 6,609,023 B1 | 8/2003 | Fischell et al. | |
| 6,612,984 B1 | 9/2003 | Kerr, II | |
| 6,616,613 B1 | 9/2003 | Goodman | |
| 6,645,154 B2 | 11/2003 | Oka | |
| 6,645,155 B2 | 11/2003 | Inukai et al. | |
| 6,652,466 B2 | 11/2003 | Sugo et al. | |
| 6,676,608 B1 * | 1/2004 | Keren | 600/481 |
| 6,678,543 B2 | 1/2004 | Diab et al. | |
| 6,681,454 B2 | 1/2004 | Modgil et al. | |
| 6,714,804 B2 | 3/2004 | Al-Ali et al. | |
| 6,723,054 B1 | 4/2004 | Baruch et al. | |
| 6,726,632 B2 | 4/2004 | Tampo | |
| 6,733,447 B2 | 5/2004 | Lai et al. | |
| 6,740,045 B2 | 5/2004 | Amano | |
| 6,775,566 B2 | 8/2004 | Nissila | |
| 6,808,473 B2 | 10/2004 | Hisano et al. | |
| 6,813,511 B2 | 11/2004 | Diab et al. | |
| 6,814,705 B2 | 11/2004 | Kawaguchi | |
| 6,852,083 B2 | 2/2005 | Caro et al. | |
| 6,871,084 B1 | 3/2005 | Kigsley et al. | |
| 2002/0183627 A1 | 12/2002 | Nishii et al. | |
| 2004/0030261 A1 | 2/2004 | Rantala | |
| 2004/0193063 A1 * | 9/2004 | Kimura et al. | 600/500 |
| 2004/0260186 A1 | 12/2004 | Dekker | |
| 2005/0131282 A1 * | 6/2005 | Brodnick et al. | 600/323 |
| 2008/0077048 A1 * | 3/2008 | Escutia et al. | 600/583 |

OTHER PUBLICATIONS

'Pulse transit time measured from the ECG: an unreliable marker of beat-to-beat blood pressure', Payne et. al, J. Appl. Physiol 100: 136-141, 2006.

Weijia Cui, Lee E. Ostrander, et al., In Vivo Reflectance of Blood and Tissue as a Function of Light Wavelength, IEEE Transactions on Biomedical Engineering, vol. 37, No. 6, pp. 632-639, 8 Pages, Jun. 1999.

* cited by examiner

BILATERAL DEVICE, SYSTEM AND METHOD FOR MONITORING VITAL SIGNS

CROSS REFERENCES TO RELATED APPLICATION

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to a method and system for measuring vital signs, and particularly blood pressure, from a patient.

2. Description of the Related Art

Pulse oximeters are medical devices featuring an optical module, typically worn on a patient's finger or ear lobe, and a processing module that analyzes data generated by the optical module. The optical module typically includes first and second light sources (e.g., light-emitting diodes, or LEDs) that transmit optical radiation at, respectively, red ($\Box$~600-700 nm) and infrared ($\Box$~800-1200 nm) wavelengths. The optical module also features a photodetector that detects transmitted radiation that passes through an underlying artery within, e.g., the patient's finger or earlobe. Typically the red and infrared LEDs sequentially emit radiation that is partially absorbed by blood flowing in the artery. The photodetector is synchronized with the LEDs to detect the transmitted radiation. In response, the photodetector generates a separate radiation-induced signal corresponding to each wavelength. The signal, called a plethysmograph, varies in a time-dependent manner as each heartbeat varies the volume of arterial blood and hence the amount of radiation absorbed along the path of light between the LEDs and the photodetector. A microprocessor in the pulse oximeter digitizes and processes plethysmographs generated by the red and infrared radiation to determine the degree of oxygen saturation in the patient's blood using algorithms known in the art. A number between 94%-100% is considered normal, while a number below 85% typically indicates the patient requires hospitalization. In addition, the microprocessor analyzes time-dependent features in the plethysmograph to determine the patient's heart rate.

Another medical device called an electrocardiograph features conductive electrodes, placed at various locations on a patient's body, that measure electrical signals which pass into an amplification circuit. The circuit generates a waveform called an electrocardiogram, or ECG, that describes a time-dependent response of the patient's cardiovascular system.

Various methods have been disclosed for using both plethysmographs and ECGs, taken alone or in combination, to measure arterial blood pressure. One such method is disclosed in U.S. Pat. No. 5,140,990 to Jones et al. The '990 Patent discloses using a pulse oximeter with a calibrated auxiliary blood pressure measurement to generate a constant that is specific to a patient's blood pressure.

Another method for using a pulse oximeter to measure blood pressure is disclosed in U.S. Pat. No. 6,616,613 to Goodman. The '613 Patent discloses processing a pulse oximetry signal in combination with information from a calibrating device to determine a patient's blood pressure.

U.S. Pat. Nos. 5,857,795 and 5,865,755 to Golub each discloses a method and device for measuring blood pressure that processes a time difference between points on an optical plethysmograph and an ECG along with a calibration signal.

U.S. Pat. No. 6,511,436 to Asmar discloses a device for evaluating arterial wall stiffness by using pulse wave velocity measurements. The device estimates blood pressure using pulse wave velocity and a patient's biometric parameters.

Chen et al, U.S. Pat. No. 6,599,251, discloses a system and method for monitoring blood pressure by detecting plethysmographs at two different locations on a subject's body, preferably on the subject's finger and earlobe. The plethysmographs are detected using conventional pulse oximetry devices and then processed to determine blood pressure.

Inukai et al., U.S. Pat. No. 5,921,936, discloses a system that uses an electrocardiogram to detect the start of a heart beat and uses a cuff equipped with a pressure sensor to detect pulse waves in order to calculate a pulse transit time.

Suda et al., U.S. Pat. No. 5,788,634, describes a multi-purpose, clip-on sensor featuring a 'gripper' that includes an electrode pair and an optical system operating in a transmission mode. The electrode pair and optical system generate information that is processed outside of the sensor to make a blood pressure measurement.

Baruch et al., U.S. Pat. No. 6,723,054, describes an arm-worn system featuring two optical systems that measure two independent signals from a patient's arm. A processor calculates mathematical derivatives of the signals to derive a pulse transit time which can be used to calculate blood pressure.

Suga et al., U.S. Pat. No. 5,316,008, describes a wrist watch that features both optical and electrical sensors for measuring signals from a patient. During operation, the patient wears the wrist watch on one wrist, and places fingers from an opposing hand on the optical and electrical sensors. A pulse transit time is extracted from the signals and then used to calculate a blood pressure.

SUMMARY OF THE INVENTION

In one aspect, the invention features a monitoring device that measures a patient's vital signs (e.g. blood pressure). The device features a first sensor configured to attach to a first portion of the patient's body (e.g. a finger). The sensor includes: i) a first electrode configured to generate a first electrical signal from the first portion of the patient's body; ii) a first light-emitting component; and iii) a first photodetector configured to receive radiation from the first portion of the patient's body and generate a first optical waveform after the radiation is emitted by the first light-emitting component. The device also features a second sensor, configured to attach to a second portion of the patient's body (e.g. a finger on the opposite hand), that includes essentially the same components. An amplifier system, in electrical contact with the first and second electrodes, receives first and second electrical signals from the two sensors to generate an electrical waveform. A processor, in electrical contact with the amplifier system, receives the electrical waveform, the first optical waveform, and the second optical waveform. The processor runs computer code that processes the input waveforms with an algorithm to determine at least one of the patient's vital signs, and most particularly blood pressure.

In embodiments, the computer code i) determines a time delay between the first optical waveform and the electrical waveform; and ii) processes the time delay to determine a blood pressure value. In other embodiments, the computer code i) determines a first time delay between the first optical waveform and the electrical waveform; ii) determines a second time delay between the second optical waveform and the electrical waveform; and iii) processes at least one (or both) of the first and second time delays to determine a blood pressure value. In still other embodiments, the computer code i) determines a time delay between the first and second optical waveforms; and ii) process the time delay to determine a blood pressure value.

In another aspect, the invention features a device for measuring a patient's vital signs (e.g., blood pressure) that includes: 1) a controller; 2) a first sensor, electrically connected to the controller by a first electrical connection and configured to clip to a first finger located on a patient's first hand; and 3) a second sensor, electrically connected to the controller by a second electrical connection and configured to clip to a second finger located on a patient's second hand. Both the first and second sensor include: i) an electrical system configured to generate an electrical signal from the inserted finger; and ii) an optical system featuring at least one light source and a photodetector and configured to generate an optical signal from the inserted finger. A processor receives a processed electrical signal generated from the first and second electrical signals and the optical signal measured from each finger, and operates computer code that processes the signals with an algorithm to determine at least one of the patient's vital signs.

In embodiments, either (or both) the first or second sensor includes an additional light-emitting component. In this case, the photodetector is typically located on a surface opposite the two light-emitting components and configured so that radiation emitted by both these components passes through the patient's finger and into the photodetector to generate separate signals. These signals, for example, can be processed by the processor to determine a pulse oximetry value. In embodiments, at least one of the light-emitting components is configured to emit infrared radiation (between, e.g., 800 and 1200 nm), red radiation (between, e.g., 600 and 700 nm), or green radiation (between, e.g., 500 and 550 nm) to generate an optical signal.

In other embodiments, one (or both) of the electrical connections is a cable, e.g. a retractable cable.

The monitor can additionally include a simple wired or wireless interface that sends vital-sign information to a personal computer. For example, the device can include a Universal Serial Bus (USB) connector that connects to the computer's back panel. Once a measurement is made, the device stores it on an on-board memory and then sends the information through the USB port to a software program running on the computer. Alternatively, the device can include a short-range radio interface (based on, e.g., Bluetooth™ or 802.15.4) that wirelessly sends the information to a matched short-range radio within the computer. The software program running on the computer then analyzes the information to generate statistics on a patient's vital signs (e.g., average values, standard deviation, beat-to-beat variations) that are not available with conventional devices that make only isolated measurements. The computer can then send the information through a wired or wireless connection to a central computer system connected to the Internet.

The central computer system can further analyze the information, e.g. display it on an Internet-accessible website. In this way medical professionals can characterize a patient's real-time vital signs during their day-to-day activities, rather than rely on an isolated measurement during a medical checkup. For example, by viewing this information, a physician can delineate between patients exhibiting white coat syndrome and patients who truly have high blood pressure. Physicians can determine patients who exhibit high blood pressure throughout their day-to-day activities. In response, the physician can prescribe medication and then monitor how this affects the patient's blood pressure.

These and other advantages of the invention will be apparent from the following detailed description and from the claims.

DETAILED DESCRIPTION OF THE INVENTION

Figure 1A:
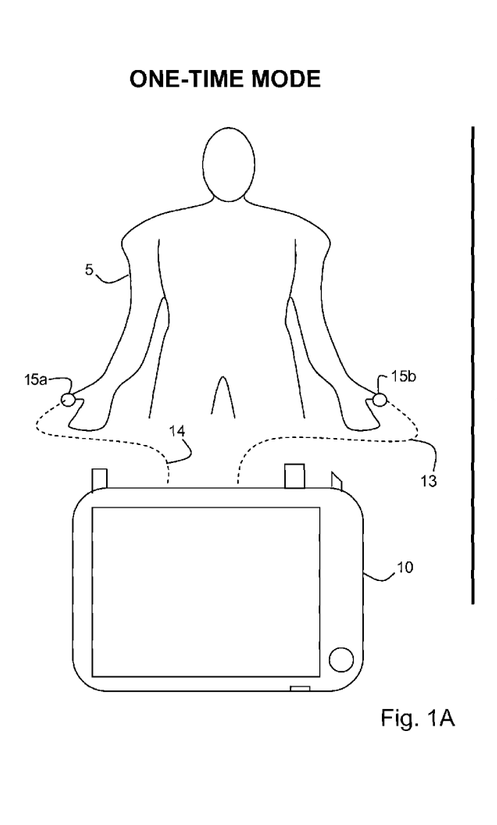
FIGS. 1A and 1B show schematic drawings of the hand-held vital sign monitor according to the invention operating in, respectively, one-time and continuous modes.
Figure 1B:
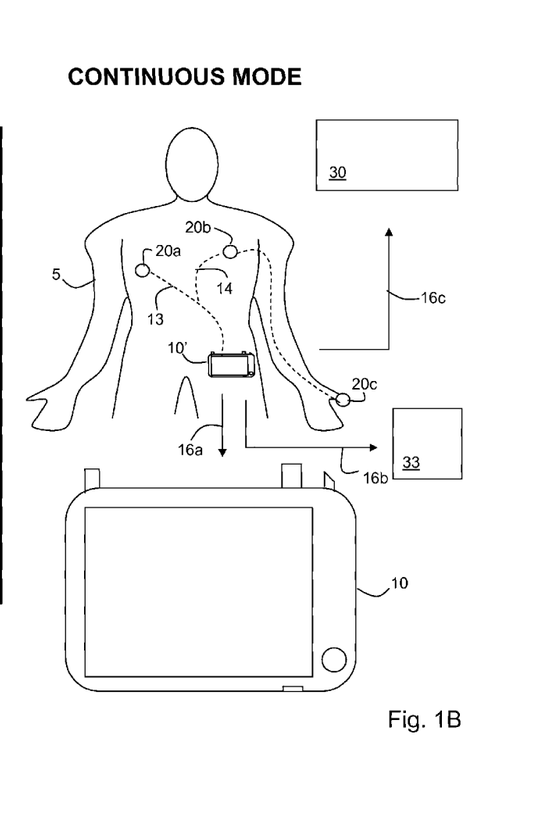

FIGS. 1A and 1B show two preferred embodiments of the invention wherein a hand-held vital sign monitor 10 measures vital sign information such as systolic and diastolic blood pressure, heart rate, pulse oximetry, temperature, ECG, and an optical plethysmograph from a patient 5. Using a 'bilateral' measurement technique described in detail below, the monitor 10 measures blood pressure values without using a conventional cuff-based system, and without requiring a complex calibration procedure. Specifically, blood pressure measurements are made with a technique referred to herein as bilateral pulse transit time, or 'BPTT', which is described in more detail in the co-pending patent application entitled 'SYSTEM FOR MEASURING VITAL SIGNS USING BILATERAL PULSE TRANSIT TIME', U.S. Ser. No. 11/420,065, filed May 26, 2006, the contents of which are incorporated herein by reference.

The same monitor 10 measures vital sign information in two different modes: 1) a one-time mode (FIG. 1A) wherein the monitor 10 makes and stores a single measurement from a patient; and 2) a continuous mode (FIG. 1B) wherein the monitor 10 periodically measures and wirelessly transmits multiple measurements from the patient over an extended period of time. In this way, a single monitor can be used in a wide variety of in-hospital settings, such as characterizing patients requiring just a single vital sign measurement (e.g., patients waiting in a medical clinic) to those requiring more sophisticated continuous monitoring (e.g., critically ill patients in a hospital telemetry ward). The monitor 10 typically features dimensions and a user interface similar to those of a conventional personal digital assistant ('PDA'), and is small enough to fit inside a medical professional's pocket or be worn on a patient's body. The monitor 10 features no cuffs and minimal external wiring to simplify operation.

In the one-time mode, two sensors 15a, 15b, each featuring a 'finger clip' form factor and described in more detail with reference to FIGS. 4, 5A, 5B, 6A, and 6B, connect through cables 13, 14 to the monitor 10. The finger clip sensors 15a, 15b feature both optical and electrical measurement systems and easily clip onto fingers on the patient's left and right hands to form a 'bilateral' configuration, described in more detail below. In this configuration, each finger clip sensor measures, respectively, optical and electrical waveforms similar to those described with reference to FIGS. 2 and 3. The optical measurement system features a common photodetector and two independent light-emitting systems: 1) an LED emitting green radiation that measures a single optical waveform in a reflection-mode geometry; and 2) a pair of LEDs emitting red and infrared radiation that measure separate optical waveforms in a transmission-mode geometry. The electrical measurement system within each finger clip sensor 15a, 15b features a single electrode, typically composed of a conventional electrode material such as brass, stainless steel, or silver/silver chloride. The electrode may additionally include an impedance-matching component, such as a conductive gel or rubber, or a disposable component.

During operation, the sensor simultaneously measures optical waveforms using both the reflection and transmission-mode optical systems, along with electrical signals using the above-described electrodes. This information passes from the sensors 15a, 15b, through the cables 13, 14, and to the monitor 10. The monitor 10 features a first amplifier system and electrical filter that processes the optical waveforms from both fingers to improve their signal-to-noise ratios, and a second amplifier system and electrical filter that processes the electrical signals from both fingers to generate a single electrical waveform, similar to a conventional single-lead ECG. An analog-to-digital converter, typically integrated within a microprocessor within the monitor, digitizes the optical and electrical waveforms to generate separate arrays of data points which can then be further processed. Specifically, computer algorithms in the monitor 10 the process the digitized optical and electrical waveforms measured in the bilateral configuration as described in more detail below to determine the patient's vital signs.

In the continuous mode, disposable adhesive patch sensors 20a, 20b, 20c attach directly to the patient's chest and arm, and connect to each other and a belt-worn monitor 10' through the cables 13, 14. The patch sensors 20a, 20b, 20c, described in more detail with reference to FIGS. 7A and 7B, include both optical and electrical measurement systems similar to the finger clip sensors described above. Specifically, the patch sensors 20a, 20b, 20c include green, red, and infrared LEDs and a common photodetector. The LEDs and photodetector are configured so that, when the patch sensor attaches to the patient's finger (e.g., patch sensor 20c), the green LED and photodetector measure an optical waveform using a reflection-mode geometry, and the red and infrared LEDs and the photodetector measure optical waveforms using a transmission-mode geometry. This geometry is shown in more detail in FIG. 8. When the patch sensor is attached to the patient's chest, the green LED and photodetector measure an optical waveform in a reflection-mode geometry, while measurements in a transmission mode geometry are typically not possible. Regardless of their positioning, electrodes within the adhesive patch sensors 20a, 20b, 20c measure electrical signals from the patient's finger and chest.

Optical waveforms and electrical signals measured by the adhesive patch sensors 20a, 20b, 20c are processed by circuitry within the belt-worn monitor 10' to determine the patient's vital signs. Both the monitor 10 and the belt-worn monitor 10' additionally include a short-range wireless system that transmits the vital signs to a number of possible devices, each of which includes a matched short-range wireless system. For example, the belt-worn monitor 10' can transmit vital sign information to: 1) the hand-held monitor 10 (as indicated by arrow 16a); 2) a remote computer 33 (as indicated by arrow 16b); or 3) a wall-mounted display 30 (e.g., an LCD or plasma screen, as indicated by arrow 16c). The belt-worn monitor 10' can transmit vital sign information in response to a command (sent, e.g., from the hand-held monitor 10), or periodically according to one or more pre-programmed values.

Figures 2A, 2B:
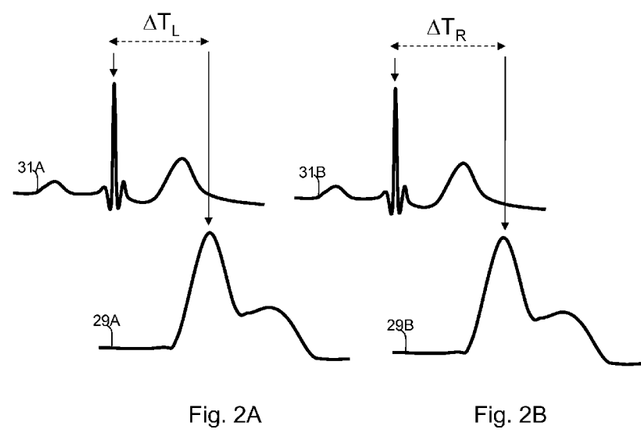
FIGS. 2A, 2B, and 2C show, respectively, graphs of optical and electrical waveforms generated with a first sensor, a second sensor, and optical waveforms generated from both the first and second sensors included in the monitor of FIGS. 1A and 1B.
Figure 2C:
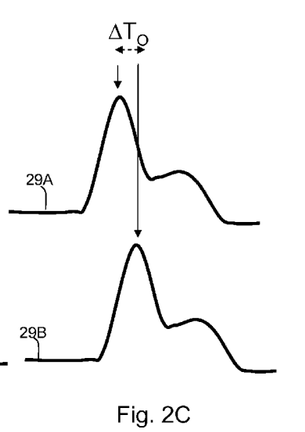

Referring to FIGS. 2A, 2B, 2C, the monitor 10 measures blood pressure using BPTT by processing optical waveforms 29A, 29B and electrical waveforms 31A, 31B measured simultaneously from each side of the patient's body. Each waveform includes a 'pulse' that corresponds to each of the patient's heartbeats. In the electrical waveforms 31A, 31B, this pulse represents electrical signals generated by the beating heart, and includes a sharply varying 'peak' within a conventional QRS complex of the ECG. In contrast, for the optical waveforms 29A, 29B, the pulse varies more gradually and represents a time-dependent volumetric change in an underlying artery. A microprocessor in the monitor 10 calculates a pulse transit time ('PTT'), described in more detail below, by analyzing a time difference $\Box T$ between a point on the optical 29A, 29B and electrical 31A, 31B waveforms (e.g., $\Box T$ between the peaks of these waveforms). Specific points on the waveforms, such as their maxima or minima, can be determined by taking a first or second derivative of the waveform. $\Box T$ measured from the optical waveform 29A from the patient's left index finger and the electrical waveform 31A is shown in FIG. 2A (labeled $\Box T_L$). Similarly, $\Box T$ measured from the optical waveform 29B from the right index finger and the electrical waveform 31B is shown in FIG. 2B (labeled $\Box T_R$).

In the one-time mode, a BPTT measurement processes PTTs measured with the finger clip sensors from the patient's left finger ($\Box T_L$) and right finger ($\Box T_R$) to make an accurate measurement of blood pressure. Specifically, PTT depends on several factors, including blood pressure, distance between the heart and the portion of the body where the optical waveform is measured (e.g., the patient's finger), and properties of the patient's vasculature (e.g., arterial compliance, size, and stiffness).

Figure 3:
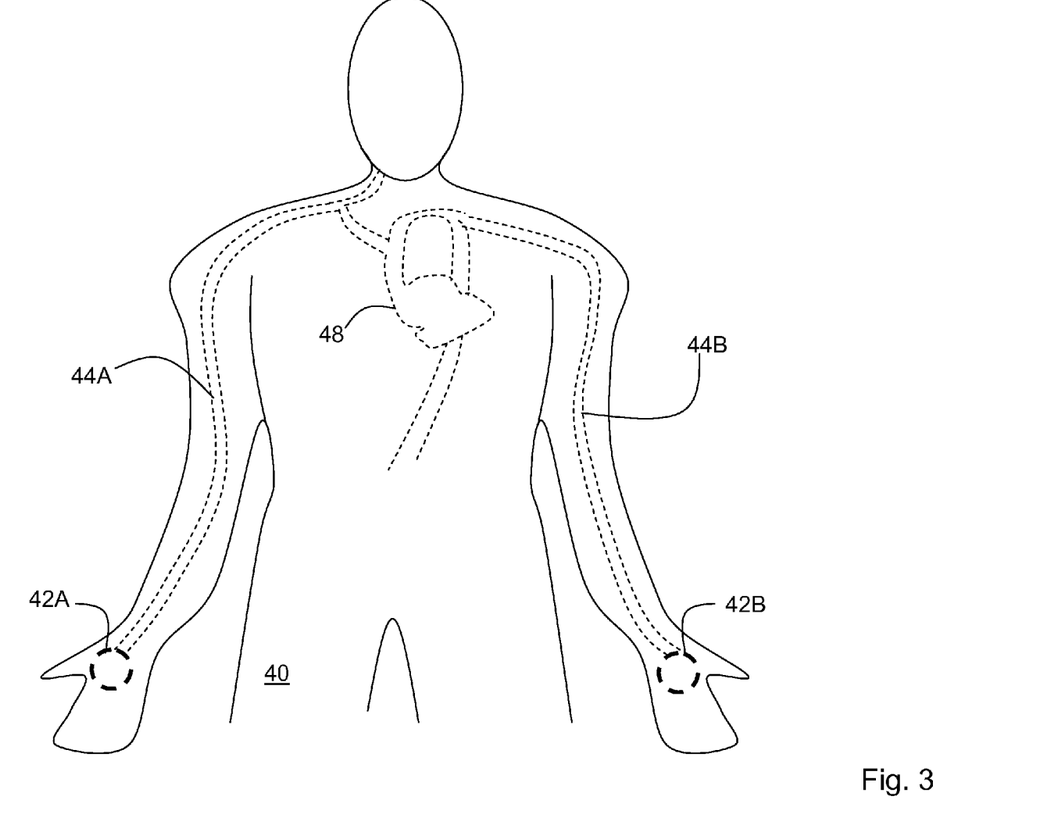
FIG. 3 shows a schematic drawing of a patient characterized by the monitor of FIGS. 1A and 1B with blood flowing on their left and right-hand sides.
Figure 4:
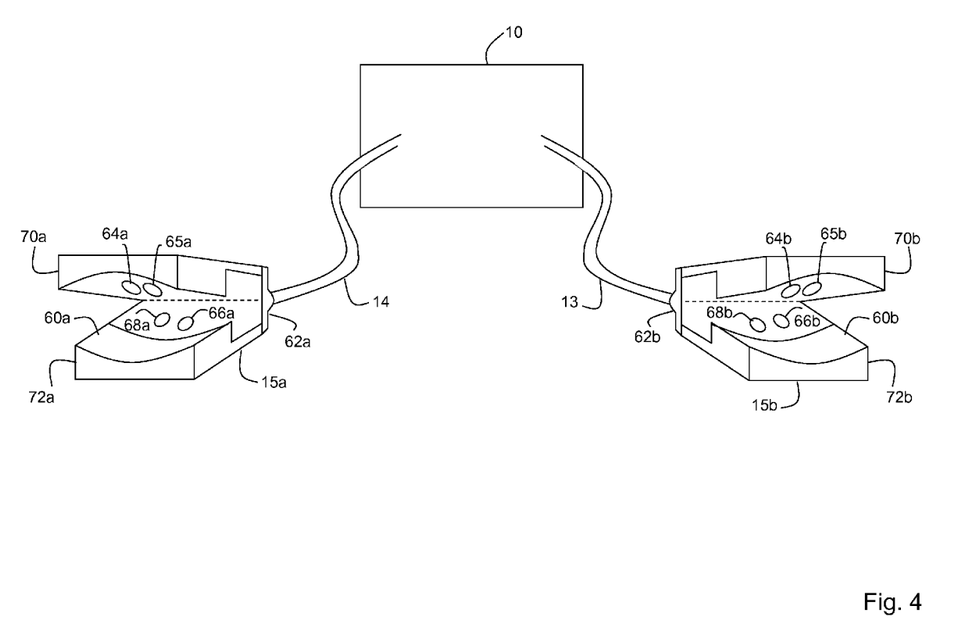
FIG. 4 shows a schematic front view of the first and second finger sensors included in the monitor of FIGS. 1A and 1B.
Figure 5A:
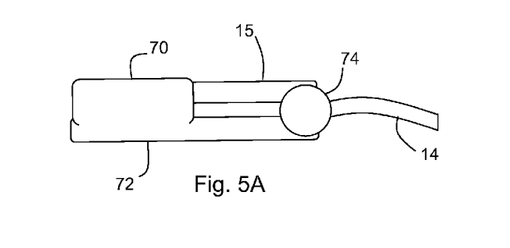
FIGS. 5A and 5B show schematic side views of the finger sensors of FIG. 4 in, respectively, open and closed configurations.
Figure 5B:
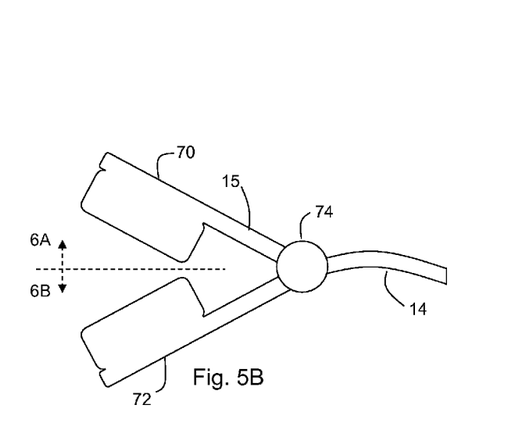
Figure 6A:
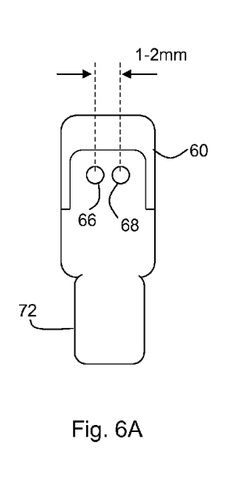
FIGS. 6A and 6B show schematic top views of, respectively, top and bottom portions of the finger sensors of FIG. 4.
Figure 6B:
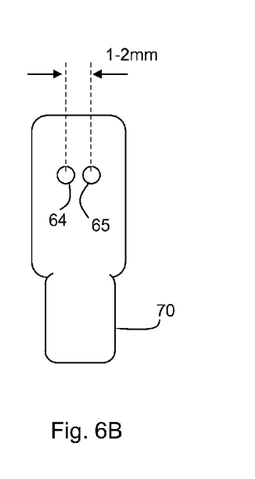

BPTT as described herein can potentially improve the accuracy of a normal PTT measurement. For example, as shown in FIG. 3, a patient's heart 48 is typically located in a relatively well-defined position on the left-hand side of their chest cavity. With each heartbeat, blood simultaneously flows along a right-hand vascular pathlength 44A to reach a point 42A on the patient's right hand, and along a left-hand vascular pathlength 44B to reach a point 42B on the patient's left hand. The right-hand vascular pathlength 44A typically differs from the left-hand vascular pathlength 44B. The difference in pathlengths can correlate with the patient's biometric parameters (e.g., height, arm span). The difference in pathlengths and corresponding difference in PTTs can be used in the calculation of the patient's vital signs (e.g., blood pressure), as is described in more detail below.

Following a heartbeat, electrical impulses travel essentially instantaneously from the patient's heart to electrodes within each finger clip or adhesive patch sensor, which detect it to generate an electrical waveform. At a later time, a pressure wave induced by the same heartbeat simultaneously propagates through the patient's right-hand 44A and left-hand 44B vascular pathlengths. At points 42A, 42B on the patient's left and right hands, elastic arteries within these vascular pathlengths increase in volume due to the pressure wave. Ultimately the pressure wave arrives at a portion of the artery underneath the LED and photodetector within each sensor. These optics combine to form an optical system that detects the pressure wave by measuring a time-dependent change in optical absorption. The propagation time of the electrical impulse is independent of blood pressure, whereas the propagation time of the pressure wave depends strongly on pressure, as well as properties of the patient's arteries.

Referring again to FIGS. 2A, 2B, and 2C, during a BPTT measurement, optical sensors within the right and left finger clip or adhesive patch sensors simultaneously measure optical waveforms 29A, 29B, while electrodes in the sensors measure electrical waveforms 31A, 31B. The optical waveforms 29A, 29B are unique to each area underneath the sensor, while the electrical waveforms 31A, 31B are identical, and are determined by combining electrical signals from multiple sensors. A microprocessor within the monitor runs an algorithm that analyzes the time difference $\Box T_{L,R}$ between the arrivals of these signals, i.e. the relative occurrence of the optical 29A, 29B and electrical 31A, 31B waveforms for both the right-hand 44A and left-hand 44B vascular system. The microprocessor additionally analyzes the time difference $\Box T_O$ between the arrival of the two optical signals 29A, 29B.

In a BPTT measurement, the asymmetric position of the heart, coupled with the assumption that blood pressure is equivalent along the left-hand 44B and right-hand 44A vascular pathlengths, means the PTT for the right-hand pathlength 44A will typically be slightly longer than the PTT for the left-hand pathlength 44B. This time difference, $\Box$PTT, is the difference between $\Box T_L$ and $\Box T_R$ (i.e. $\Box$PTT=$\Box T_R$−$\Box T_L$) and can be used to estimate the patient's arm length if a speed of the propagating pressure pulse, called a pulse wave velocity ('PWV') is assumed. Inclusion of arm length in a PTT-based measurement typically improves accuracy for both systolic and diastolic blood pressure. Use of BPTT to determine $\Box$PTT means arm length can be estimated without having to enter it through a software user interface. Alternatively, the arm length can be entered into a user interface associated with the monitor, and then processed along with $\Box$PTT to calculate a PWV. This is done by using the above-described assumptions describing the asymmetrical position of the heart. Blood pressure is known to depend strongly on PWV (typically an increase in PWV indicates an increase in blood pressure), and thus a measured PWV value can be compared to a look-up table stored in memory to calculate blood pressure. Alternatively, a mathematical algorithm, such as a predetermined relationship (e.g., a linear relationship) between PWV and blood pressure, may be used to calculate subsequent blood pressure values.

Referring to FIG. 2C, in another embodiment the time difference $\Box T_O$ between points (e.g., peaks) on two optical signals measured at different locations on the patient's body can be processed to determine a PWV. For example, separate patch sensors 20b, 20c located, respectively, on the patient's chest and finger can measure the arrival of a pulse wave following each heart beat. As described above, the distance between the patch sensors 20b, 20c divided by the time difference $\Box T_O$ yields a PWV, which can then be compared to a look-up table stored in memory or processed with a more sophisticated algorithm to calculate blood pressure. For example, the algorithm may use a predetermined relationship (e.g. a linear relationship) between PWV and blood pressure to calculate subsequent blood pressure values.

In addition, with the BPTT measurement, optical waveforms measured from the patient's left and right hands or $\Box$PTT can be compared to determine slight differences in waveform shape. These slight differences can then be processed to achieve a more accurate calculation of the patient's blood pressure. For example, the differences in left and right waveform shapes or arrival times measured as described above can be used to determine a particular mathematical model for calculating blood pressure from a patient, or alternatively properties other than blood pressure. An abnormally high or negative $\Box$PTT, for example, may indicate a profound difference between a patient's right-hand 44A and left-hand 44B vascular pathlength. Such a difference, for example, may indicate the presence of an occlusion (e.g., a blood clot) or stenosis in either vascular pathlength. In related embodiments, the $\Box$PTT or waveform shape differences may be used to estimate a patient's arterial compliance. For example, the differences in the patient's right-hand 44A and left-hand 44B vascular pathlengths will result in corresponding differences in the diffusion of light-absorbing blood cells in the two pathlengths. These differences in cellular diffusion are observed as differences in the shapes of the optical waveforms 29A and 29B. The waveform shape differences will depend on the arterial compliance along the right-hand 44A and left-hand 44B vascular pathlengths. For example, the optical signals (29A, 29B) shown in FIGS. 2A, 2B, 2C typically feature a main peak and a secondary peak, where the secondary peak is typically classified as a 'dichrotic notch'. Studies published in the literature describe how the dichrotic notch, particularly when analyzed by taking a second derivative of the plethysmogram, relates to vascular compliance (see, e.g., 'Assessment of Vasoactive Agents and Vascular Aging by the Second Derivative of Photoplethysmogram Waveform', Takazawa et. al, Hypertension 32: 365-370, 1998; the contents of which are incorporated herein by reference). Arterial compliance determined using this or another method can then be used to group patients having similar arterial properties. An algorithm can then process $\Box$PTT or PWV values for patients in a particular group, or compare these values to predetermined look-up tables, to make a blood pressure measurement. For example, the algorithm may use a predetermined relationship (e.g. a linear relationship) between PWV or $\Box$PTT and blood pressure to calculate subsequent blood pressure values.

Referring again to FIGS. 2A, 2B, and 2C, in yet another embodiment, processing the electrical waveform 31A, 31B and optical waveforms 29A, 29B can be used to estimate a property called pre-ejection period ('$\Box T_{PEP}$'), which is the time delay between the beginning of a patient's heart beat and the beginning of the patient's cardiac stroke. Specifically, both $\Box T_R$ and $\Box T_L$ depend on $\Box T_{PEP}$ and the time it takes the pressure pulse to leave the heart and arrive at the optical system underneath a corresponding sensor. As shown in FIG. 2C, this time difference, referred to as $\Box T_O$, can be measured directly from patch sensors located near the patient's heart and finger. If the patch sensor is located on the patient's right hand, $\Box T_R$−$\Box T_O$=$\Box T_{PEP}$, while if the patch sensor is located on the patient's left hand $\Box T_L$−$\Box T_O$=$\Box T_{PEP}$. $\Box T_{PEP}$ correlates with the patient's systolic function, with a shorter $\Box T_{PEP}$ typically indicating a relatively healthy systolic function. A measured $\Box T_{PEP}$ can be used in conjunction with the time difference between a feature on the electrical waveform and one or more features on one or more optical waveforms to improve the accuracy of the calculated PTT and corresponding blood pressure. In particular, it has been shown in previous studies that systolic blood pressure can correlate better to a $\Box$PTT value, whereas diastolic blood pressure and mean arterial blood pressure can correlate better to a $\Box$PTT value corrected for $\Box T_{PEP}$, i.e. $\Box$PTT−$\Box T_{PEP}$ (see, e.g., 'Pulse transit time measured from the ECG: an unreliable marker of beat-to-beat blood pressure', Payne et. al, J. Appl. Physiol 100: 136-141, 2006; the contents of which are incorporated herein by reference). $\Box T_{PEP}$ values may also vary with respiration and inspiration, thereby affecting the measured blood pressure. For this reason, in embodiments, computer code operating in the monitor described above can first process two optical waveforms to estimate $\Box T_{PEP}$. Once this is done, the computer code can determine $\Box$PTT and $\Box$PTT−$\Box T_{PEP}$, which are then used to calculate, respectively, systolic and diastolic blood pressure.

FIGS. 4, 5A, 5B, 6A, and 6B show the above-described finger clip sensors 15a, 15b of FIG. 1A in more detail. As described above, finger clips sensors 15a, 15b are typically used in a one-time measurement mode. Each finger clip sensor 15a, 15b is designed to gently clip onto an index finger on the patient's left and right hands, and features a top portion 70a, 70b connected to a bottom portion 72a, 72b by a spring-loaded backing portion 62a, 62b. This configuration ensures that, during operation, each finger clip sensor secures to the patient's finger and blocks out ambient light, thereby increasing the signal-to-noise ratio of both the optical and electrical measurements. As described above, the bottom portion 72a, 72b features an electrode material 60a, 60b that contacts a bottom portion of the patient's finger when the finger clip sensor is closed. The electrode material 60a, 60b is typically a metal, such as brass or copper, or a conventional electrode such as silver/silver chloride. The electrode material 60a, 60b may also include an impedance-matching material, such as a conductive gel or rubber. Electrical signals measured with electrode materials 60a, 60b from the left 15a and right 15b finger clip sensors pass through cables 13, 14 to the monitor, where they are processed with an amplifier circuit and then digitized to generate an electrical waveform similar to a conventional ECG. Unlike the optical waveforms, which specifically correspond to each blood flowing in each index finger, a single electrical waveform is determined by jointly processing electrical signals measured from each index finger using the amplifier circuit.

The bottom portion 72a, 72b of the finger clip sensor 15a, 15b additionally includes a photodiode 66a, 66b and a green LED 68a, 68b disposed on the same surface, and typically separated from each other by about 1-2 mm. During operation, radiation from the green LED 68a, 68b reflects off the patient's finger and its underlying arteries to generate reflected radiation, which the photodiode 66a, 66b detects to generate a time-dependent optical waveform. This waveform is measured in a reflection-mode geometry, and because it is not used to calculate pulse oximetry, can typically be measured at a relatively high frequency (e.g., several kHz) and resolution (8-16-bit). Typically the photodiode 66a, 66b and green LED 68a, 68b are seated below a soft rubber material so that they don't make direct contact with skin on the bottom surface of the patient's finger. The top portion 70a, 70b includes a red LED 64a, 64b and an infrared LED which sequentially emit radiation that, during operation, transmits through the patient's index finger and its underlying arteries. Some radiation that passes through the arteries exposes the photodiode 66a, 66b, which in response generates a pair of time-dependent optical waveforms (one from each of the red and infrared LEDs). These waveforms are measured in a transmission-mode geometry. During operation, the optical waveforms measured in both transmission and reflection modes pass through the cables 13, 14 to the monitor, where they are processed as described above to measure the patient's vital signs. Blood pressure values are calculated as described above. Heart rate values can be calculated by processing the optical and electrical waveforms using techniques known in the art. Pulse oximetry values can be calculated by collectively processing waveforms generated by the red and infrared LEDs using techniques know in the art.

Figure 7A:
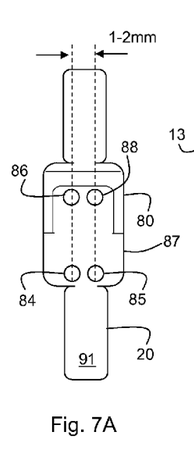
FIGS. 7A and 7B show schematic top views of, respectively, top and bottom portions of a patch sensor used in place of the finger sensors of FIG. 4.
Figure 7B:
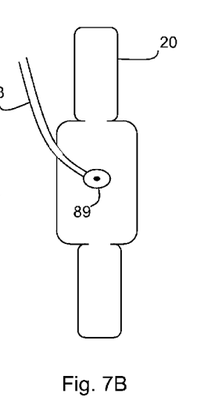
Figures 8, 9:
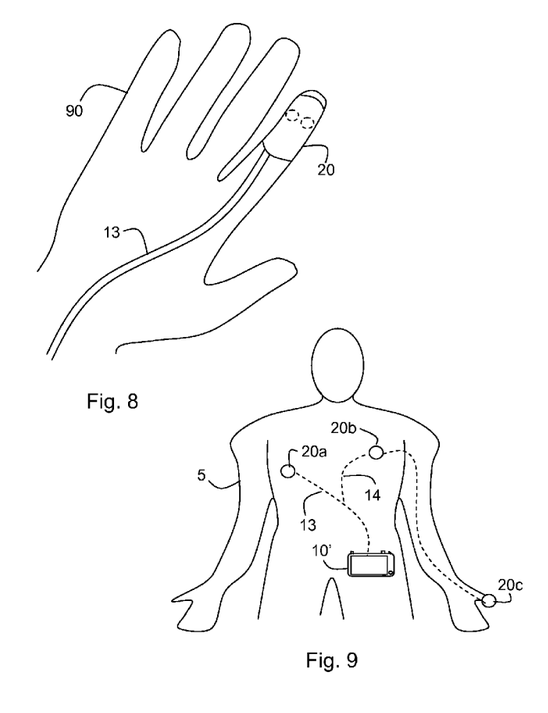
FIG. 8 shows a schematic view of the patch sensor of FIGS. 7A and 7B attached to the patient's hand.
FIG. 9 shows a schematic view of three patch sensors of FIGS. 7A and 7B attached to the patient's body.

FIGS. 7A, 7B, 8 and 9 show the adhesive patch sensors 20a, 20b, 20c of FIG. 1B in more detail. As described above, the adhesive patch sensors 20a, 20b, 20c are typically used in a continuous measurement mode. Each sensor features a green LED 88 positioned proximal to a photodiode 86, both of which are disposed on a flexible printed circuit board 87. When the sensor is attached to a patient, these optical components generate an optical waveform as described above. A horseshoe-shaped metal electrode 80 formed on top of the flexible printed circuit board 87 surrounds these optical components and generates an electrical signal that, when processed in concert with another electrical signal from a separate electrode, generates an electrical waveform. Red 84 and infrared 85 LEDs are additionally mounted on an opposite end of the flexible printed circuit board. When the sensor is attached to a patient's finger, as shown in FIG. 8, the red 84 and infrared 85 LEDs generate radiation that passes through the finger and into the photodiode 86, as described above, to generate separate optical waveforms in a transmission-mode geometry. On its outer surface the sensor includes a snap connector 89 that allows it to easily attach and detach to a cable 13. All electrical signals and optical waveforms, once generated, pass through the cable 13 to the monitor, which analyzes them as described above to measure a patient's vital sign information. The patch sensor 20 additionally features an adhesive component 91, similar to that in a common band-aid or ECG electrode, which adheres to the patient's skin and secures the sensor in place to minimize the effects of motion.

Both the cable 13 and snap connector 89 include matched electrical leads that supply power and ground to the LEDs 84, 85, 88, photodetector 86, and electrode 80. When the patch sensor 20 is not measuring optical and electrical waveforms, the cable 13 unsnaps from the snap connector 89, while the sensor 20 remains adhered to the patient's skin. In this way a single sensor can be used for several days. After use, the patient removes and then discards the sensor 20.

Figure 10A:
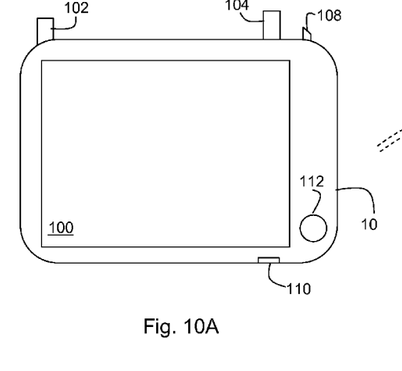
FIGS. 10A and 10B show schematic views of, respectively, front and back surfaces of the monitor of FIGS. 1A and 1B.
Figure 10B:
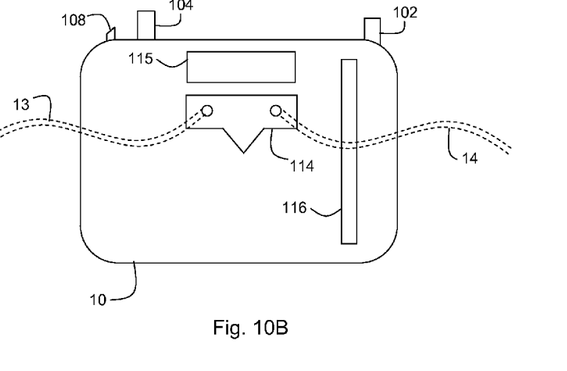

FIGS. 10A and 10B show, respectively, front and back surfaces of the monitor 10. The front surface (FIG. 10A) features a touch-screen display 100 rendering a graphical user interface that operates in both one-time and continuous modes. A removable stylus 108 is housed in a slot on a top surface of the monitor and is used to operate the user interface through the touch-screen display 100. The monitor 10 typically includes separate antennae 102, 104 for, respectively, short-range communications (for, e.g., part-15 or 802.11-based networks) and long-range communications (for, e.g., CDMA networks). The antenna 102 for short-range communication typically communicates with peripheral devices, such as the belt-worn monitor, a wireless scale, chest strap, thermal printer, external monitor, or local personal computer. The antenna 104 for long-range communications is typically used to send information through a wireless network to an Internet-based computer system. The monitor also includes an on/off button 112 and a USB connector 110 for downloading information to a personal computer and recharging the monitor's battery through a cable.

On its back surface (FIG. 10B) the monitor 10 includes a mechanical mechanism 114 that retracts both cables 13, 14 when they're not in use. In this way the monitor can be kept as compact as possible with minimal external components. Alternatively, the mechanical mechanism 114 can be replaced with a simple connector that mates with a connector terminating both cables 13, 14. In other embodiments, the monitor can also include a bar code scanner 115 that reads conventional bar-coded information from, e.g., a patient's wrist band. Typically the bar code scanner 115 connects to a microprocessor through a serial interface. In other embodiments, a thermometer 116 for measuring body temperature connects to the monitor 10 through either a wired or wireless interface.

Figure 11:
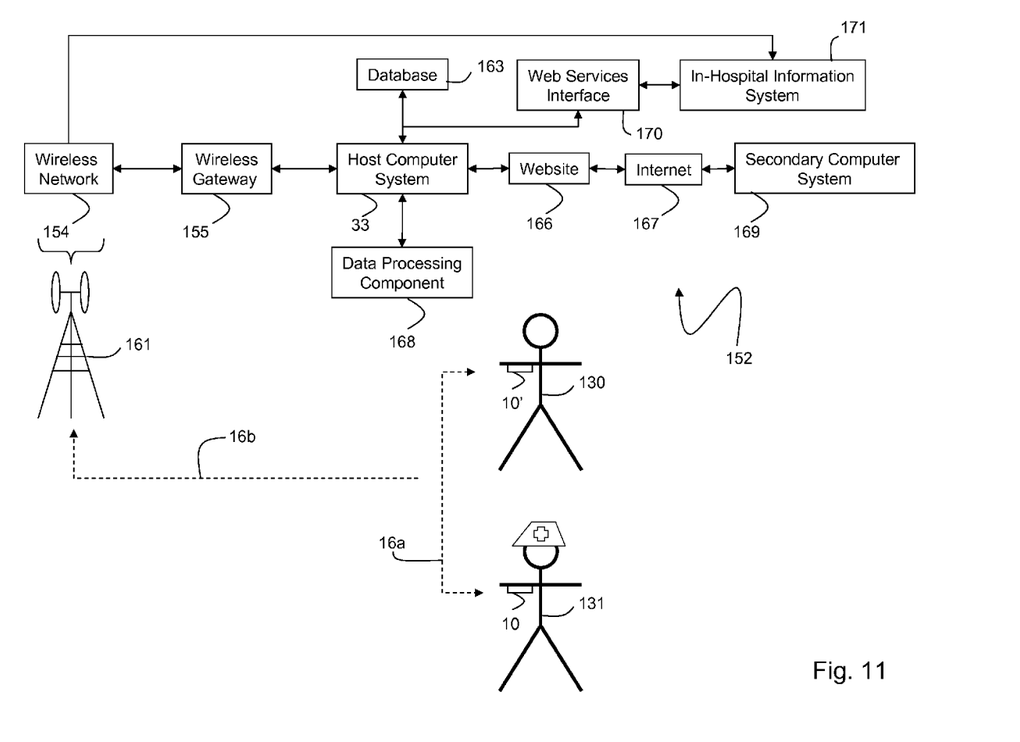
FIG. 11 shows a schematic drawing of an in-hospital information system operating with the monitor of FIGS. 1A and 1B.

FIG. 11 shows a preferred embodiment of an Internet-based system 152 that operates in concert with the hand-held monitor 10 and body-worn monitor 10' to send information from a patient 130 to an in-hospital information system 171. Using the hand-held monitor 10, a medical professional 131 collects vital sign information from the patient's body-worn monitor 10' through a short-range wireless connection 16a. Alternatively, the body-worn monitor 10' automatically transmits vital sign information in a continuous or near-continuous manner. In both cases, using an internal wireless modem, information travels from either the hand-held monitor 10 or body-worn monitor 10' through a wireless interface 16b to a wireless network 154 (e.g., either a nation-wide or local wireless network), and from there to a web site 166 hosted on an Internet-based host computer system 33. A secondary computer system 169 accesses the website 166 through the Internet 167. A wireless gateway 155 connects to the host computer system 33 and ultimately to the wireless network 154, and receives data from one or more monitors, as discussed below. The host computer system 33 includes a database 163 and a data-processing component 168 for, respectively, storing and analyzing data sent from the monitor. The host computer system 33, for example, may include multiple computers, software systems, and other signal-processing and switching equipment, such as routers and digital signal processors. The wireless gateway 155 preferably connects to the wireless network 154 using a TCP/IP-based connection, or with a dedicated, digital leased line (e.g., a VPN, frame-relay circuit or digital line running an X.25 or other protocols). The host computer system 33 also hosts the web site 166 using conventional computer hardware (e.g. computer servers for both a database and the web site) and software (e.g., web server and database software). To connect to the in-hospital information system 171 (e.g., a system for electronic medical records), the host computer system 33 typically includes a web services interface 170 that sends information using an XML-based web services link to a computer associated with the in-hospital information system 171. Alternatively, the wireless network 154 may be an in-hospital wireless network (e.g., a network operating Bluetooth™, 802.11a, 802.11b, 802.1g, 802.15.4, or 'mesh network' wireless protocols) that connects directly to the in-hospital information system 171. In this embodiment, a nurse working at a central nursing station can quickly view the vital signs of the patient using a simple computer interface.

To view information remotely, the patient or medical professional can access a user interface hosted on the web site 166 through the Internet 167 from a secondary computer system 169, such as an Internet-accessible home computer. The system may also include a call center, typically staffed with medical professionals such as doctors, nurses, or nurse practitioners, whom access a care-provider interface hosted on the same website 166.

Other embodiments are also within the scope of the invention. For example, PTT can be used to first determine mean arterial pressure (MAP) as opposed to systolic blood pressure (BP SYS) or diastolic blood pressure (BP DIA). In this case, a predetermined relationship between PTT and MAP is established. In subsequent measurements, PTT is measured and used to calculate MAP. The optical waveform can then be analyzed to estimate pulse pressure (i.e., BP SYS–BP DIA), which can then be used along with MAP to estimate both BP SYS and BP DIA using the formula:

$$MAP = BP\ SYS + \frac{1}{3}(BP\ SYS - BP\ DIA)$$

In still other embodiments, the body-worn monitor can optionally be used to determine the patient's location using embedded position-location technology (e.g., GPS, network-assisted GPS, or Bluetooth™, 802.11-based location system). In situations requiring immediate medical assistance, the patient's location, along with relevant vital sign information, can be relayed to emergency response personnel.

Still other embodiments are within the scope of the following claims.

We claim as our invention:

1. A monitoring device for measuring a patient's vital signs, said monitoring device comprising:

a first sensor configured to attach to a first portion of the patient's body, comprising: i) a first electrode configured to generate a first electrical signal from the first portion of the patient's body; ii) a first light-emitting component; and iii) a first photodetector configured to receive radiation from the first portion of the patient's body after the radiation is emitted by the first light-emitting component and in response generate a first optical waveform;

a second sensor configured to attach to a second portion of the patient's body, comprising: i) a second electrode configured to generate a second electrical signal from the second portion of the patient's body; ii) a second light-emitting component; and iii) a second photodetector configured to receive radiation from the second portion of the patient's body after the radiation is emitted by the second light-emitting component and in response generate a second optical waveform;

an amplifier system, in electrical contact with the first and second electrodes, configured to process the first and second electrical signals to generate an electrical waveform; and, a processor, in electrical contact with the amplifier system, configured to receive the electrical waveform or a processed version thereof, the first optical waveform or a processed version thereof, and the second optical waveform or a processed version thereof, the processor comprising computer code which, when executed by the processor causes the processor to process the received electrical waveform or a processed version thereof and the received optical waveforms or processed versions thereof with an algorithm to determine at least one of the patient's vital signs, wherein said computer code is configured to: i) determine an overall time delay between the first optical waveform or a processed version thereof and the second optical waveform or a processed version thereof; and ii) process the overall time delay to determine a blood pressure value, wherein the processor further comprises computer code which, when executed by the processor, causes the computer to: i) determine a first time delay between the first optical waveform or the processed version thereof and the received electrical waveform or the processed version thereof; and ii) process the first time delay to determine a blood pressure value.

2. A monitoring device, for measuring a patient's vital signs, said monitoring device comprising:
a first sensor configured to attach to a first portion of the patient's body, comprising: i) a first electrode configured to generate a first electrical signal from the first portion of the patient's body; ii) a first light-emitting component and iii) a first photodetector configured to receive radiation from the first portion of the patient's body after the radiation is emitted by the first light-emitting component and in response generate a first optical waveform;
a second sensor configured to attach to a second portion of the patient's body, comprising: i) a second electrode configured to generate a second electrical signal from the second portion of the patient's body; ii) a second light-emitting component and iii) a second photodetector configured to receive radiation from the second portion of the patient's body after the radiation is emitted by the second light-emitting component and in response generate a second optical waveform;
an amplifier system, in electrical contact with the first and second electrodes, configured to process the first and second electrical signals to generate an electrical waveform; and,
a processor, in electrical contact with the amplifier system, configured to receive the electrical waveform or a processed version thereof, the first optical waveform or a processed version thereof, and the second optical waveform or a processed version thereof, the processor comprising computer code which, when executed by the processor causes the processor to process the received electrical waveform or a processed version thereof and the received optical waveforms or processed versions thereof with an algorithm to determine at least one of the patient's vital signs, wherein said computer code is configured to: i) determine an overall time delay between the first optical waveform or a processed version thereof and the second optical waveform or a processed version thereof; and ii) process the overall time delay to determine a blood pressure value, wherein the processor further comprises computer code which, when executed by the processor, causes the computer to: i) determine a first time delay between the first optical waveform or the processed version thereof and the received electrical waveform or the processed version thereof; ii) determine a second time delay between the second optical waveform or the processed version thereof and the received electrical waveform or the processed version thereof; and iii) process at least one of the first and second time delays to determine a blood pressure value.

3. A monitoring device, for measuring a patient's vital signs, said monitoring device comprising:
a first sensor configured to attach to a first portion of the patient's body, comprising: i) a first electrode configured to generate a first electrical signal from the first portion of the patient's body; ii) a first light-emitting component and iii) a first photodetector configured to receive radiation from the first portion of the patient's body after the radiation is emitted by the first light-emitting component and in response generate a first optical waveform;
a second sensor configured to attach to a second portion of the patient's body, comprising: i) a second electrode configured to generate a second electrical signal from the second portion of the patient's body; ii) a second light-emitting component and iii) a second photodetector configured to receive radiation from the second portion of the patient's body after the radiation is emitted by the second light-emitting component and in response generate a second optical waveform;
an amplifier system, in electrical contact with the first and second electrodes, configured to process the first and second electrical signals to generate an electrical waveform; and,
a processor, in electrical contact with the amplifier system, configured to receive the electrical waveform or a processed version thereof, the first optical waveform or a processed version thereof, and the second optical waveform or a processed version thereof, the processor comprising computer code which, when executed by the processor causes the processor to process the received electrical waveform or a processed version thereof and the received optical waveforms or processed versions thereof with an algorithm to determine at least one of the patient's vital signs, wherein said computer code is configured to: i) determine an overall time delay between the first optical waveform or a processed version thereof and the second optical waveform or a processed version thereof; and ii) process the overall time delay to determine a blood pressure value, wherein the processor further comprises computer code which, when executed by the processor, causes the computer to: i) determine a first time delay between the first optical waveform or the processed version thereof and the received electrical waveform or the processed version thereof; ii) determine a second time delay between the second optical waveform or the processed version thereof and the received electrical waveform or the processed version thereof; and iii) process both the first and second time delays to determine a blood pressure value.

4. A monitoring device, for measuring a patient's vital signs, said monitoring device comprising:
a first sensor configured to attach to a first portion of the patient's body, comprising: i) a first electrode configured to generate a first electrical signal from the first portion of the patient's body; ii) a first light-emitting component and iii) a first photodetector configured to receive radiation from the first portion of the patient's body after the radiation is emitted by the first light-emitting component and in response generate a first optical waveform;
a second sensor configured to attach to a second portion of the patient's body, comprising: i) a second electrode configured to generate a second electrical signal from the second portion of the patient's body; ii) a second light-emitting component and iii) a second photodetector configured to receive radiation from the second portion of the patient's body after the radiation is emitted by the second light-emitting component and in response generate a second optical waveform;
an amplifier system, in electrical contact with the first and second electrodes, configured to process the first and second electrical signals to generate an electrical waveform; and,
a processor, in electrical contact with the amplifier system, configured to receive the electrical waveform or a processed version thereof, the first optical waveform or a processed version thereof, and the second optical waveform or a processed version thereof, the processor comprising computer code which, when executed by the processor causes the processor to process the received electrical waveform or a processed version thereof and the received optical waveforms or processed versions thereof with an algorithm to determine at least one of the patient's vital signs, wherein said computer code is configured to: i) determine an overall time delay between the first optical waveform or a processed version thereof and the second optical waveform or a processed version thereof; and ii) process the overall time delay to determine a blood pressure value, wherein the processor further comprises computer code which, when executed by the processor, causes the computer to measure blood pressure by:

1) determining at least one of the following: i) a first time delay between the first optical waveform or the processed version thereof and the received electrical waveform or the processed version thereof; and ii) a second time delay between the second optical waveform or the processed version thereof and the received electrical waveform or the processed version thereof; and
2) processing at least one of the first and second time delays to determine a blood pressure value.

5. A device for measuring a patient's vital signs, said device comprising:
   a first sensor configured to attach to a first portion of the patient's body, comprising: i) a first electrode configured to generate a first electrical signal from the first portion of the patient's body; ii) a first light-emitting component; and iii) a first photodetector configured to receive radiation from the first portion of the patient's body after the radiation is emitted by the first light-emitting component and in response generate a first optical signal;
   a second sensor configured to attach to a second portion of the patient's body, comprising: i) a second electrode configured to generate a second electrical signal from the second portion of the patient's body; ii) a second light-emitting component; and iii) a second photodetector configured to receive radiation from the second portion of the patient's body after the radiation is emitted by the second light-emitting component and in response generate a second optical signal; and,
   a processor configured to receive a processed electrical signal generated from the first and second electrical signals or a processed version thereof, the first optical signal or a processed version thereof, and the second optical signal or a processed version thereof, the processor comprising computer code which, when executed by the processor causes the processor to process the received processed electrical signal and the received optical signals or processed versions thereof with an algorithm to determine at least one of the patient's vital signs, wherein said computer code is configured to: i) determine an overall time delay between the first optical signal or a processed version thereof and the second optical signal or a processed version thereof, and ii) process the overall time delay to determine a blood pressure value, wherein the processor further comprises computer code which, when executed by the processor, causes the computer to: i) determine a first time delay between the first optical signal or the processed version thereof and the processed electrical signal; and ii) process the first time delay to determine a blood pressure value.

6. A device for measuring a patient's vital signs, said device comprising:
   a first sensor configured to attach to a first portion of the patient's body, comprising: i) a first electrode configured to generate a first electrical signal from the first portion of the patient's body; ii) a first light-emitting component and iii) a first photodetector configured to receive radiation from the first portion of the patient's body after the radiation is emitted by the first light-emitting component and in response generate a first optical signal;
   a second sensor configured to attach to a second portion of the patient's body, comprising: i) a second electrode configured to generate a second electrical signal from the second portion of the patient's body; ii) a second light-emitting component; and iii) a second photodetector configure to receive radiation from the second portion of the patient's body after the radiation is emitted by the second light-emitting component and in response generate a second optical signal; and,
   a processor configured to receive a processed electrical signal generated from the first and second electrical signals or a processed version thereof, the first optical signal or a processed version thereof, and the second optical signal or a processed version thereof, the processor comprising computer code which, when executed by the processor causes the processor to process the received processed electrical signal and the received optical signals or processed versions thereof with an algorithm to determine at least one of the patient's vital signs, wherein said computer code is configured to: i) determine an overall time delay between the first optical signal or a processed version thereof and the second optical signal or a processed version thereof, and ii) process the overall time delay to determine a blood pressure value, wherein the processor further comprises computer code which, when executed by the processor, causes the computer to: i) determine a first time delay between the first optical signal or the processed version thereof and the processed electrical signal; ii) determine a second time delay between the second optical signal or the processed version thereof and the processed electrical signal; and ii) process at least one of the first and second time delays to determine a blood pressure value.

7. A device for measuring a patient's vital signs, said device comprising:
   a first sensor configured to attach to a first portion of the patient's body, comprising: i) a first electrode configured to generate a first electrical signal from the first portion of the patient's body; ii) a first light-emitting component and iii) a first photodetector configured to receive radiation from the first portion of the patient's body after the radiation is emitted by the first light-emitting component and in response generate a first optical signal;
   a second sensor configured to attach to a second portion of the patient's body, comprising: i) a second electrode configured to generate a second electrical signal from the second portion of the patient's body; ii) a second light-emitting component and iii) a second photodetector configured to receive radiation from the second portion of the patient's body after the radiation is emitted by the second light-emitting component and in response generate a second optical signal; and,
   a processor configured to receive a processed electrical signal generated from the first and second electrical signals or a processed version thereof, the first optical signal or a processed version thereof, and the second optical signal or a processed version thereof, the processor comprising computer code which, when executed by the processor causes the processor to process the received processed electrical signal and the received optical signals or processed versions thereof with an algorithm to determine at least one of the patient's vital signs, wherein said computer code is configured to: i) determine an overall time delay between the first optical signal or a processed version thereof and the second optical signal or a processed version thereof, and ii) process the overall time delay to determine a blood pressure value, wherein the processor further comprises computer code which, when executed by the processor, causes the computer to: i) determine a first time delay between the first optical signal or the processed version thereof and the processed electrical signal; ii) determine a second time delay between the second optical signal or the processed version thereof and the processed electrical signal; and ii) process both the first and second time delays to determine a blood pressure value.

8. A device for measuring a patient's vital signs, said device comprising:
a first sensor configured to attach to a first portion of the patient's body, comprising: i) a first electrode configured to generate a first electrical signal from the first portion of the patient's body; ii) a first light-emitting component and iii) a first photodetector configured to receive radiation from the first portion of the patient's body after the radiation is emitted by the first light-emitting component and in response generate a first optical signal;
a second sensor configured to attach to a second portion of the patient's body, comprising: i) a second electrode configured to generate a second electrical signal from the second portion of the patient's body; ii) a second light-emitting component and iii) a second photodetector configured to receive radiation from the second portion of the patient's body after the radiation is emitted by the second light-emitting component and in response generate a second optical signal; and,
a processor configured to receive a processed electrical signal generated from the first and second electrical signals or a processed version thereof, the first optical signal or a processed version thereof, and the second optical signal or a processed version thereof, the processor comprising computer code which, when executed by the processor causes the processor to process the received processed electrical signal and the received optical signals or processed versions thereof with an algorithm to determine at least one of the patient's vital signs, wherein said computer code is configured to: i) determine an overall time delay between the first optical signal or a processed version thereof and the second optical signal or a processed version thereof, and ii) process the overall time delay to determine a blood pressure value, wherein the processor further comprises computer code which, when executed by the processor, causes the computer to measure blood pressure by:
1) determining at least one of the following: i) a first time delay between the first optical signal or the processed version thereof and the processed electrical signal; and ii) a second time delay between the second optical signal or the processed version thereof and the processed electrical signal; and
2) processing at least one of the first and second time delays to determine a blood pressure value.

9. A device for measuring a patient's vital signs, said device comprising:
a controller;
a first sensor, electrically connected to the controller by a first electrical connection and configured to clip to a first finger located on a patient's first hand, comprising: i) a first electrical system configured to generate a first electrical signal from the first finger; and ii) a first optical system comprising at least one light source and a photodetector and configured to generate a first optical signal from the first finger;
a second sensor, electrically connected to the controller by a second electrical connection and configured to clip to a second finger located on a patient's second hand, comprising: i) a second electrical system configured to generate a second electrical signal from the second finger; and ii) a second optical system comprising at least one light source and a photodetector and configured to generate a second optical signal from the second finger; and,
a processor configured to receive a processed electrical signal generated from the first and second electrical signals or a processed version thereof, the first optical signal or a processed version thereof, and the second optical signal or a processed version thereof, the processor comprising computer code which, when executed by the processor causes the processor to process the received electrical signal and the received optical signals with an algorithm to determine at least one of the patient's vital signs, wherein said computer code is configured to: i) determine an overall time delay between the first optical signal or a processed version thereof and the second optical signal or a processed version thereof, and ii) process the overall time delay to determine a blood pressure value, wherein the processor further comprises computer code which, when executed by the processor, causes the computer to: i) determine a first time delay between the first optical waveform or the processed version thereof and the received electrical waveform or the processed version thereof; and ii) process the first time delay to determine a blood pressure value.

10. The device of claim 9, wherein the first sensor further comprises a third light-emitting component.

11. The device of claim 10, wherein the first and third light-emitting components are comprised by the first sensor, and the photodetector is located on a surface located opposite the first and third light-emitting components and configured so that radiation emitted by both the first and third light-emitting components passes through the patient's first finger and into the photodetector to generate first and third optical signals.

12. The device of claim 11, wherein the processor wherein the processor further comprises computer code which, when executed by the processor, causes the computer to process the first optical signal or a processed version thereof in combination with the third optical signal or a processed version thereof to determine a pulse oximetry value.

13. The device of claim 11, wherein the second sensor further comprises a fourth light-emitting component.

14. The device of claim 13, wherein the second and fourth light-emitting components are comprised by the second sensor, and the photodetector is comprised by a second surface of the second housing, the second surface located opposite the first surface and configured so that radiation emitted by the second and fourth light-emitting components passes through the patient's second finger and into the photodetector to generate the second and fourth optical signals.

15. The device of claim 9, further comprising a first light-emitting component configured to emit infrared radiation.

16. The device of claim 15, further comprising a first light-emitting component configured to emit radiation having a wavelength between 800 and 1200 nm.

17. The vital sign monitor of claim 15, wherein the first light-emitting component is connected to the first housing on a first surface, and the photodetector is connected to the first housing on a second surface, the first surface configured to face the second surface so that infrared radiation passes through the first finger and irradiates the photodetector to generate the first optical signal.

18. The device of claim 9, further comprising a first light-emitting component configured to emit green radiation.

19. The device of claim 18, further comprising a first light-emitting component configured to emit radiation having a wavelength between 500 and 550 nm.

20. The device of claim 18, wherein the first light-emitting component and the photodetector are connected to the first housing on a first surface and configured so that green radiation reflects off the first finger and irradiates the photodetector to generate the first optical signal.

21. The device of claim 9, wherein at least one of the first or second electrical connections is a cable.

22. The device of claim 21, wherein the controller further comprises a mechanism for retracting at least one of the cable or cables.

* * * * *